(12) United States Patent
Gonzales et al.

(10) Patent No.: US 11,406,734 B2
(45) Date of Patent: *Aug. 9, 2022

(54) MALLEABLE DEMINERALIZED BONE COMPOSITION AND METHOD OF MANUFACTURE

(71) Applicant: Vivex Biologics Group, Inc., Atlanta, GA (US)

(72) Inventors: Silvia Daniela Gonzales, Miami, FL (US); Shabnam Namin, Miami, FL (US); Timothy Ganey, Tampa, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/071,660

(22) Filed: Oct. 15, 2020

(65) Prior Publication Data

US 2021/0023271 A1    Jan. 28, 2021

Related U.S. Application Data

(63) Continuation of application No. 16/701,709, filed on Dec. 3, 2019, now Pat. No. 11,253,630, which is a
(Continued)

(51) Int. Cl.
*A61F 2/02* (2006.01)
*A61F 2/00* (2006.01)
(Continued)

(52) U.S. Cl.
CPC .......... *A61L 27/3608* (2013.01); *A61F 2/02* (2013.01); *A61L 2/087* (2013.01); *A61L 27/222* (2013.01);
(Continued)

(58) Field of Classification Search
None
See application file for complete search history.

(56) References Cited

U.S. PATENT DOCUMENTS

| 3,458,397 A | 7/1969 | Myers et al. |
| 4,172,128 A | 10/1979 | Thiele et al. |

(Continued)

FOREIGN PATENT DOCUMENTS

| WO | WO-9938543 A2 * | 8/1999 | ............... A61F 2/28 |

OTHER PUBLICATIONS

Chu Chang Chua, Deborah Ceiman, and Roger L. Ladda; "Transforming Growth Factors Released From Kirsten Sarcoma Virus Transformed Cells Do Not Compete for Epidermal Growth Factor Membrane Receptors"; Journal of Cellular Physiology 117:116-122 (1983).

(Continued)

*Primary Examiner* — Ann Schillinger
(74) *Attorney, Agent, or Firm* — David L. King

(57) ABSTRACT

A malleable demineralized bone composition consists of cortical bone made from a first portion and a second portion. The first portion and second portion of cortical bone is made from cut pieces freeze dried then ground into particles and demineralized then freeze-dried. A volume of the second portion is placed in a solution of sterile water to create a mixture, the water volume being seven times the volume of the second portion, the mixture is autoclaved under heat and pressure to form a gelatin, and the first portion is mixed with the gelatin to form a malleable putty or paste.

2 Claims, 5 Drawing Sheets

Related U.S. Application Data continuation-in-part of application No. 15/136,301, filed on Apr. 22, 2016, now Pat. No. 10,596,298.

(51) Int. Cl.

| | | |
|---|---|---|
| *A61L 27/36* | (2006.01) | |
| *A61L 27/22* | (2006.01) | |
| *A61L 2/08* | (2006.01) | |
| *A61K 35/32* | (2015.01) | |
| *A61L 27/54* | (2006.01) | |
| *A61F 2/28* | (2006.01) | |

(52) U.S. Cl.
CPC .............. *A61L 27/365* (2013.01); *A61L 27/54* (2013.01); *A61F 2002/2835* (2013.01); *A61F 2210/0004* (2013.01); *A61L 2400/06* (2013.01); *A61L 2430/02* (2013.01)

(56) References Cited

U.S. PATENT DOCUMENTS

| | | | |
|---|---|---|---|
| 4,440,750 | A | 4/1984 | Glowacki et al. |
| 5,073,373 | A | 12/1991 | Oleary et al. |
| 5,236,456 | A | 8/1993 | Oleary et al. |
| 5,486,359 | A | 1/1996 | Caplan et al. |
| 5,490,937 | A | 2/1996 | vanReis |
| 5,531,791 | A | 7/1996 | Wolfinbarger |
| 5,733,542 | A | 3/1998 | Haynesworth et al. |
| 6,432,436 | B1 | 8/2002 | Gertzman et al. |
| 6,437,018 | B1 | 8/2002 | Gertzman et al. |
| 6,458,375 | B1 | 10/2002 | Gertzman et al. |
| 6,576,249 | B1 | 6/2003 | Gendler et al. |
| RE38,522 | E | 5/2004 | Gertzman et al. |
| 6,911,212 | B2 | 6/2005 | Gertzman et al. |
| 6,998,135 | B1 | 2/2006 | Sunwoo et al. |
| 7,015,037 | B1 | 3/2006 | Furcht et al. |
| 7,019,192 | B2 | 3/2006 | Gertzman et al. |
| 7,045,141 | B2 | 5/2006 | Merboth et al. |
| 7,067,123 | B2 | 6/2006 | Gomes et al. |
| RE39,587 | E | 4/2007 | Gertzman et al. |
| 7,488,348 | B2 | 2/2009 | Truncale et al. |
| 7,659,118 | B2 | 2/2010 | Furcht et al. |
| 7,824,702 | B2 | 11/2010 | Wironen |
| 7,847,072 | B2 | 12/2010 | Thorne |
| 7,879,103 | B2 | 2/2011 | Gertzman et al. |
| RE42,208 | E | 3/2011 | Truncale et al. |
| 7,901,457 | B2 | 3/2011 | Truncale et al. |
| 8,075,881 | B2 | 12/2011 | Verfaillie et al. |
| RE43,258 | E | 3/2012 | Truncale et al. |
| 8,202,539 | B2 * | 6/2012 | Behnam .............. A61L 27/3683 |
| | | | 424/549 |
| 8,221,500 | B2 | 7/2012 | Truncale et al. |
| 8,292,968 | B2 | 10/2012 | Truncale et al. |
| 8,354,370 | B2 | 1/2013 | Kopen et al. |
| 8,357,384 | B2 * | 1/2013 | Behnam .............. A61L 27/3834 |
| | | | 424/549 |
| 8,394,419 | B2 | 3/2013 | Borden |
| 8,834,928 | B1 | 9/2014 | Truncale et al. |
| 9,138,508 | B2 | 9/2015 | Borden |
| 9,138,509 | B2 | 9/2015 | Sunwoo et al. |
| 9,192,695 | B2 | 11/2015 | Shi |
| 9,554,920 | B2 * | 1/2017 | Wei .................... A61L 27/3608 |
| 10,123,876 | B2 * | 11/2018 | Namin ..................... A61L 27/50 |
| 10,357,593 | B2 * | 7/2019 | Maldonado ......... A61L 27/3683 |
| 2002/0192266 | A1 | 12/2002 | Merboth |
| 2003/0059414 | A1 | 3/2003 | Ho et al. |
| 2004/0058412 | A1 | 3/2004 | Ho et al. |
| 2004/0097612 | A1 | 5/2004 | Rosenberg |
| 2005/0181502 | A1 | 8/2005 | Furcht et al. |
| 2006/0004189 | A1 | 1/2006 | Gandy |
| 2006/0083769 | A1 * | 4/2006 | Kumar ................ A61L 27/3683 |
| | | | 424/549 |
| 2006/0204544 | A1 * | 9/2006 | Sunwoo .............. A61L 27/3608 |
| | | | 424/549 |
| 2006/0280803 | A1 * | 12/2006 | Kumar .................. A61L 27/365 |
| | | | 424/549 |
| 2007/0049739 | A1 | 3/2007 | Troxel |
| 2007/0524177 | | 9/2007 | Ho et al. |
| 2008/0281431 | A1 * | 11/2008 | Missos .................. A61L 27/427 |
| | | | 623/23.6 |
| 2009/0227704 | A1 * | 9/2009 | Troxel ...................... A61F 2/28 |
| | | | 523/115 |
| 2012/0121660 | A1 * | 5/2012 | Akella ................ A61L 24/0084 |
| | | | 424/549 |
| 2013/0195810 | A1 | 8/2013 | Crawford et al. |
| 2014/0005793 | A1 | 1/2014 | Koford et al. |
| 2014/0010890 | A1 * | 1/2014 | Borden ................ A61L 27/507 |
| | | | 424/549 |
| 2014/0030235 | A1 | 1/2014 | Varney et al. |
| 2015/0012107 | A1 | 1/2015 | Koford et al. |
| 2016/0030639 | A1 | 2/2016 | Shi |
| 2016/0296668 | A1 | 10/2016 | Burden |
| 2020/0101197 | A1 * | 4/2020 | Gonzales .................. A61F 2/28 |

OTHER PUBLICATIONS

Yawei Liu,A, Anders Kalenb, Olof Ristob & ; "Time- and pH-dependent release of PDGF and TGF-ß from platelets&It;emph type="2">in vitro&It;/emph>"; pp. 233-237 Platelets vol. 14, Issue 4, 2003 ; Published online: Jul. 7, 2009.

Trinity Elite, product, sales brochure, TT-1515, Orthofix Holdings Inc, Oct. 2015.

Osteocel bone graft web page, http://www.nuvasive.com/patient-solutions/nuvasive-integrated-surgical-solutions/osteocel-bone-graft/; 2016.

* cited by examiner

MALLEABLE DEMINERALIZED BONE COMPOSITION AND METHOD OF MANUFACTURE

RELATED APPLICATIONS

This application is a continuation of co-pending U.S. application Ser. No. 16/701,709 filed on Dec. 3, 2019 which is a continuation in part of U.S. application Ser. No. 15/136,301 filed Apr. 22, 2016, now U.S. Pat. No. 10,596,298 issued on Mar. 24, 2020 entitled, "Malleable Demineralized Bone Composition And Method Of Manufacture".

TECHNICAL FIELD

This invention is a malleable demineralized bone composition. More specifically, a composition that can be formed as a flowable paste or a molded shape retaining structure and a method of manufacture and use of said composition.

BACKGROUND OF THE INVENTION

The manufacture and use of bone allografts from bone tissue is well known. The use of particles of various specific sizes and distributions have been determined to have beneficial characteristics for new bone growth in the treatment of osseous defects and bone voids.

The issue of getting the repair composition to stay in position has been addressed for various formulations made into malleable paste or putty by the addition of collagen or other gelatinous materials.

The present invention provides an improvement over those prior art materials.

SUMMARY OF THE INVENTION

A malleable demineralized bone composition consists of cortical bone made from a first portion and a second portion. The first and second portions of cortical bone are made from cut pieces freeze dried then ground into particles and demineralized then freeze-dried. A volume of the second portion is placed in a solution of sterile water to create a mixture, the water volume being seven times the second portion, the mixture is autoclaved under heat and pressure to form a gelatin, and the first portion is mixed with the gelatin to form a malleable putty or paste.

The freeze-dried DBM particles are ground to a particle size up to 300 microns. The cut pieces having a width, a length and a thickness in the range of 1 to 4 mm, the pieces are freeze-dried and ground to form the cortical bone ground particles of the first portion that are less than 1000 microns and greater than 100 microns. In a preferred embodiment, the ground particles are sieved to a first size range of 106 to 300 microns.

The malleable demineralized bone composition has a ratio of gelatin from the second portion to particles from the first portion of 80:20 by volume when mixed together. The mixture forms a malleable putty or paste which can be packaged in a capped syringe. The packaged mixture is stored at room temperature.

A method of making a malleable demineralized bone composition consisting of cortical bone comprises the steps of: preparing cortical bone by cutting the cortical bone into pieces, freeze-drying the pieces and then grinding into particles and demineralizing the ground particles and the freeze-drying the demineralized ground particles to form freeze-dried DBM particles; dividing the freeze-dried DBM particles into first and second portions wherein cortical bone plates are cut into long pieces, cleaned and then freeze-dried, grinding the freeze-dried pieces to obtain a particle size less than 300 microns and demineralizing the particles thereafter freeze-drying to form the freeze-dried DBM particles; autoclaving a volume of the second portion of DBM particles mixed with sterile water in a 7:1 ratio by volume for a predetermined time at a pre-set temperature and pressure to form a gelatin; cooling the gelatin made from the second portion; and mixing the freeze-dried ground particles of the first portion with the gelatin from the second portion at a ratio of 80:20 or less gelatin to DBM to create a malleable putty or paste.

Definitions

Cohesiveness is defined as the capacity of DBM aseptic paste to maintain its shape while immersed in normal saline or water for a minimum of one minute.

DBM—Demineralized Bone Matrix.

Cryopreserved—Tissue frozen with the addition of, or in a solution containing, a cryoprotectant agent.

Freeze Dried/Lyophilized—Tissue dehydrated for storage by conversion of the water content of frozen tissue to a gaseous state under vacuum that extracts moisture.

Malleability is the ability of DBM aseptic paste to be molded into different shapes with no visible cracks.

Normal Saline—0.9% Sodium Chloride Solution.

PBS—Phosphate Buffered Saline.

SRI—an equipment sterilization company.

BRIEF DESCRIPTION OF THE DRAWINGS

The invention will be described by way of example and with reference to the accompanying drawings in which.

DETAILED DESCRIPTION OF THE INVENTION

The present invention encompasses the manufacturing of a Demineralized Bone Matrix (DBM) aseptic paste or putty derived from human cadaveric cortical bone. Cortical bone is obtained from male or female donors within suitable age groups. Full body donors with no joint replacements are preferred. The donors' medical and social history are screened for medical conditions such as osteoporosis and alcohol abuse, which may hinder the intended purpose of the final product. The demineralization process of bone tissue exposes morphogenetic proteins and other intrinsic growth factors involved in providing the osteoinductive signal to form new bone. Therefore, the application of DBM aseptic paste products is intended to aid in the treatment of osseous defects and bone voids. DBM aseptic paste or putty is ready for implantation and does not require preoperative preparation such as thawing or mixing. At room temperature, DBM aseptic paste or putty is moldable and cohesive.

Figure 1:
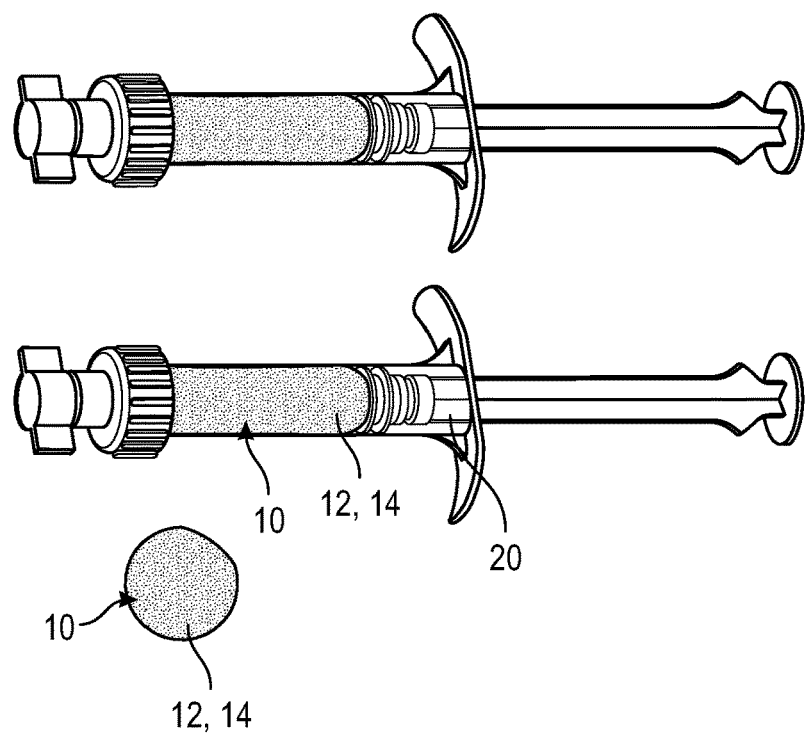
FIG. 1 shows a photograph of the malleable demineralized bone composition rolled into a "ball" like shape in the foreground and two composition filled syringes in the background.
Figure 2:
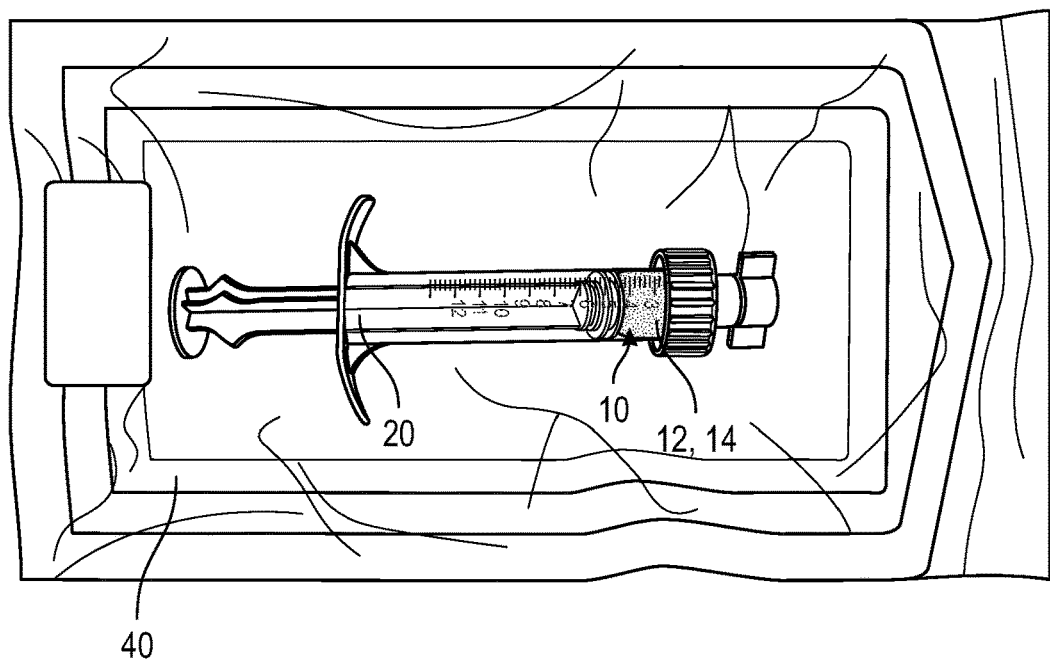
FIG. 2 is a photograph of one composition filled syringe packaged in a clear sealed bag.

The DBM paste or putty product is entirely derived from aseptic allograft cortical bone. The cortical bone is aseptically cleaned, cut, morselized or shaved, ground, sieved at different sizes, demineralized and freeze dried to obtain cortical bone particles. Gelatin is obtained from freeze dried ground cortical bone mixed with water. DBM aseptic paste or putty is prepared by mixing ground cortical bone particles and gelatin. As shown in FIG. 1, final DBM aseptic paste or putty 10 products of 1, 5 or 10 cc are distributed into syringes 20 of 3 or 14 ml, packaged in final packaging 40, as shown in FIG. 2, and stored at room temperature until distribution to the end user. To ensure the osteoinductive potential of the final product, every lot of demineralized particulate tissue used to prepare DBM aseptic paste is tested in vitro using the C2C12 differentiation assay, which has been shown to have a positive correlation with results obtained in vivo.

Figure 3:
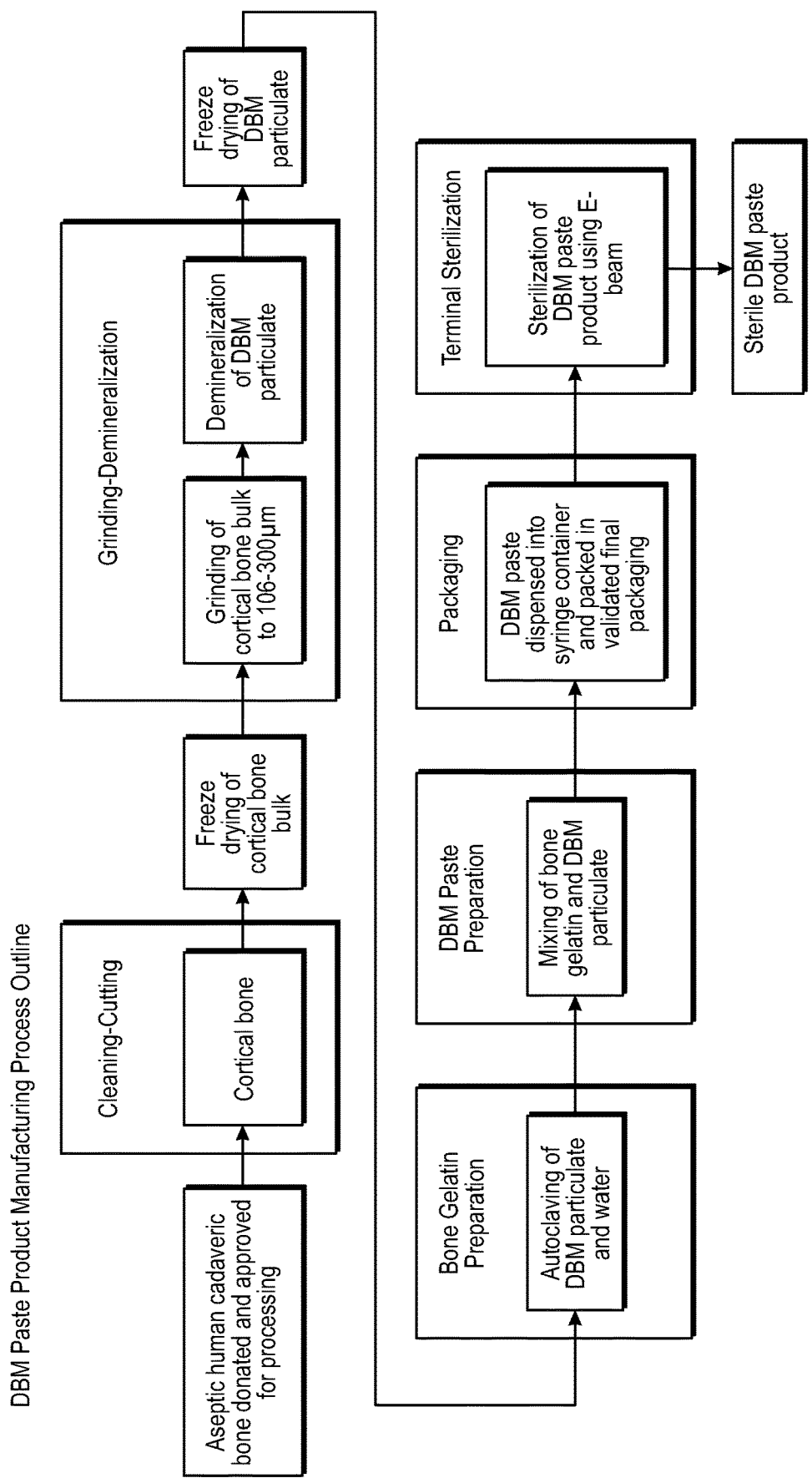
FIG. 3 is a schematic outline of the overall manufacture process.

FIG. 3 is an outline of the overall manufacturing process. FIGS. 4-8 are each of the subprocesses.

Figure 4:
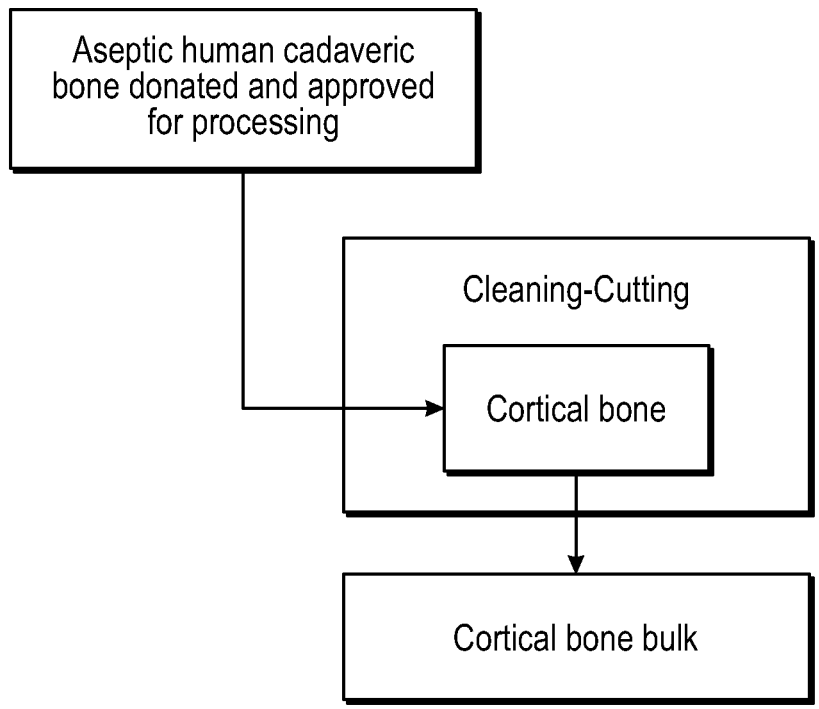
FIG. 4 is the subprocess of cutting taken from FIG. 3.

With reference to FIG. 4, the subprocess of cutting is schematically shown. Prior to cutting the donated and approved for processing aseptic human cadaveric cortical bone, all extraneous material such as muscle fibers, adipose tissue, and periosteum are removed from the tissue. Bones are then rinsed a minimum of 3 times with physiological grade normal saline (0.9% Sodium Chloride). Using a band saw, the bones are cut in a manner that the cortical and cancellous portions are separated. Cortical bone shafts are cut in half longitudinally and placed in basins with normal saline. Further cleaning and cutting of cortical bone is divided into 2 subprocesses forming a first and second portion of the composition 10, as detailed below.

Cortical bone bulk makes up the first portion 12 of the composition 10. Cortical bone plates are cut into small pieces using a band saw. The small pieces are rinsed a minimum of three times in normal saline and then placed into a metal container with normal saline. The container is wrapped, placed on a shaker and mechanically agitated for 5 to 10 minutes. The bone tissue is then morselized into 1 to 4 mm length and width pieces using a morselizer. The tissue is rinsed a minimum of three times with normal saline in order to remove any remnants of blood and/or fat deposits. The bone pieces are rinsed with hydrogen peroxide if required for no more than 10 minutes to remove fat/blood. The bone pieces are rinsed a minimum of three times with sterile water to remove any residual hydrogen peroxide. Then, the bone tissue is placed in a metal cube, stored at −80° C. and then freeze dried. The freeze drying cycle is set to run for 33 hours 50 minutes. It is understood the timing, ratios and volumes can vary based on the equipment and procedures used and the above is exemplary of the preferred process for the inventors' equipment.

Cortical bone bulk also makes up the second portion 14 of the composition 10. Cortical bone plates are cut into approximately 6.5 cm long pieces. The bone plates are placed in a wash can with normal saline. The wash can is wrapped and agitated for 5 to 10 minutes to remove any blood and adipose tissue. Bone tissues are then rinsed with normal saline as often as needed to clean tissue of blood and/or fatty deposits. The bone tissue pieces are collected in a basin and rinsed with hydrogen peroxide if required for no more than 10 minutes to remove fat/blood if necessary. Cortical bone particles are rinsed a minimum of three times with sterile water to remove any residual hydrogen peroxide. The particles are stored at −80° C. and then freeze dried. The freeze drying cycle is set to run for 33 hours 50 minutes. It is understood the timing, ratios and volumes can vary based on the equipment and procedures used and the above is exemplary of the preferred process for the inventors' equipment.

Figure 5:
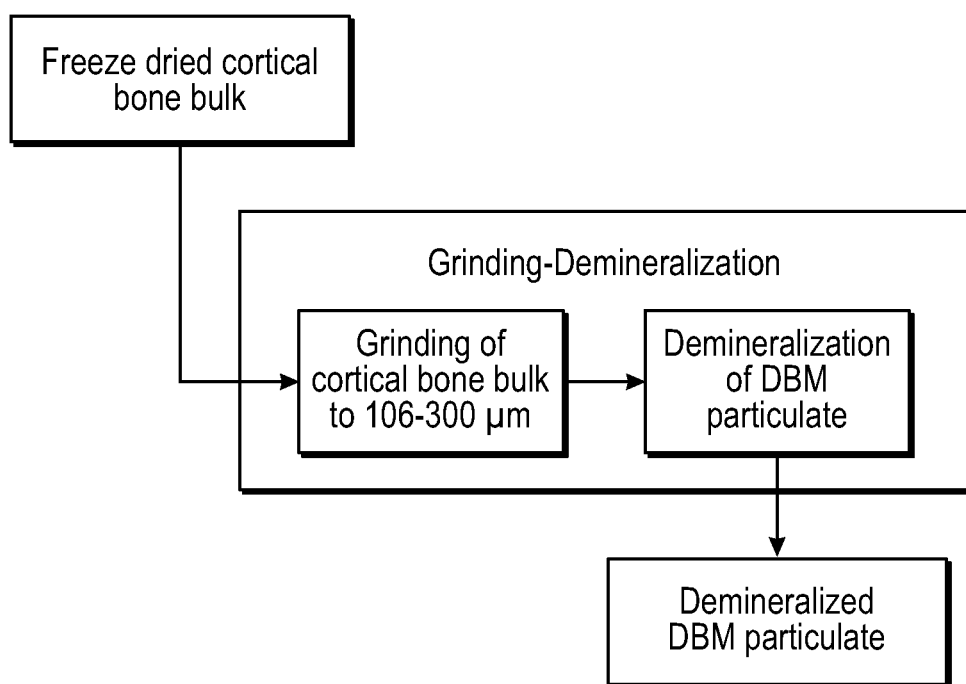
FIG. 5 is the subprocess of grinding and demineralizing taken from FIG. 3.

As shown in FIG. 5, the next subprocess is grinding-demineralization.

Further processing of cortical bone is detailed below.

The cortical bone bulk pieces; once the freeze drying cycle is completed, the cortical bone bulk pieces are ground and sieved to obtain particle sizes of 106 to 300 µM. Then, the particulate tissue is mixed with 0.6 HCL solution at a 20:1 ratio (20 ml of 0.6 HCL to 1 g of bone). The solution containing the tissue is placed on a magnetic stir plate for 19 minutes. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the particulate tissue is mixed with sterile water at a 20:1 ratio (20 ml of sterile water to 1 g of bone). The solution containing the tissue is placed on a magnetic stir plate for 9 minutes. The water waste solution is decanted and the demineralized particulate tissue is stored at −80° C. The demineralized particulate tissue is freeze dried for 33 hours 50 minutes. At the end of the freeze drying process, a sample is collected for Residual Moisture testing.

The grinding-demineralization process of the first portion 12 of the composition 10 is similarly conducted. Cortical bone mix; once the freeze drying cycle is completed, the cortical bulk is ground and sieved to obtain particle sizes of 100 to 300 microns. Then, the mix of particulate tissue at different sizes is mixed with 0.7 HCL solution at a 20:1 ratio (20 ml of 0.7 HCL to 1 g of bone). The solution containing the tissue is placed on a magnetic stir plate for 59 minutes. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the particulate tissue is mixed with sterile water at a 20:1 ratio (20 ml of sterile water to 1 g of bone). The solution containing the tissue is placed on a magnetic stir plate for 9 minutes. The water waste solution is decanted and the demineralized particulate tissue (DBM mix) is stored at −80° C. The DBM mix is freeze dried for 33 hours 50 minutes. At the end of the freeze drying process, samples are collected for residual moisture, residual calcium and osteoinduction testing.

Figure 6:
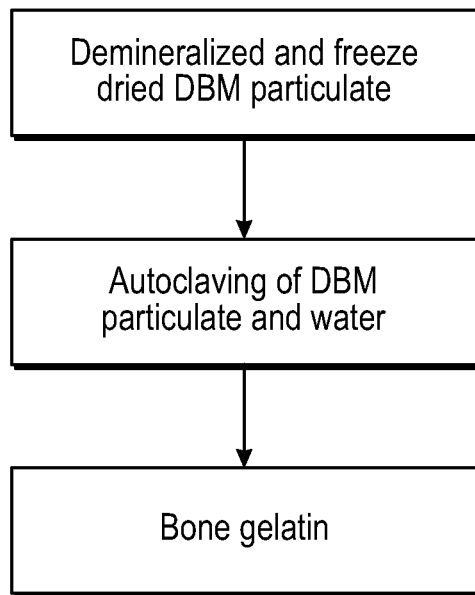
FIG. 6 is the subprocess of gelatin preparation taken from FIG. 3.

The next subprocess, shown in FIG. 6, is gelatin preparation. Gelatin preparation and DBM Aseptic Paste Preparation processes are contingent upon positive osteoinduction testing results of the DBM mix. For gelatin preparation, freeze-dried DBM particles are divided into groups of 100 cc, approximately. Each group is placed in a Pyrex glass bottle and mixed with sterile water. The ratio of sterile water to particles is 7:1 by volume. This ratio can be varied up or down by adjusting times to accommodate the altered ratios. In order to prepare gelatin, the mix is autoclaved for 1.25 hours. The autoclaving process includes conditioning (15 minutes), exposure (30 minutes) and drying (30 minutes) steps. Temperature during the exposure step is 121.1° C. and the pressure is 30.15 psi. After autoclaving is completed, the gelatin is allowed to cool down to 37° C. in an incubator.

Figure 7:
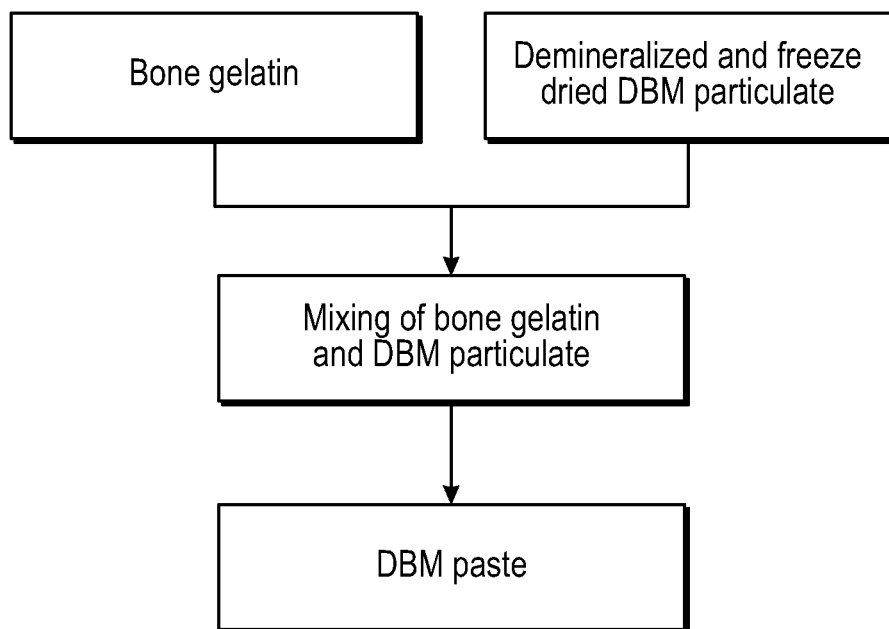
FIG. 7 is the subprocess of paste preparation taken from FIG. 3.

As shown in FIG. 7, DBM aseptic paste preparation is described below.

DBM aseptic paste is prepared by mixing freeze-dried DBM mix with gelatin, which must not exceed 40° C. before mixing. The ratio of gelatin to DBM mix is 80:20 by volume, respectively. The DBM paste is distributed into 3 ml or 14 ml syringes (1, 5 or 10 cc of product). The syringes are capped immediately after the DBM product is put in the syringe. Surrogate samples of DBM aseptic paste are used for liquid culture sterility testing. Quality Control tests of malleability and cohesiveness are performed using a DBM aseptic paste sample after a minimum of 5 days of preparation. Malleability is the ability of DBM aseptic paste to be molded into different shapes with no visible cracks. Cohesiveness is defined as the capacity of DBM aseptic paste to maintain its shape while immersed in normal saline or water for a minimum of one minute.

Figure 8:
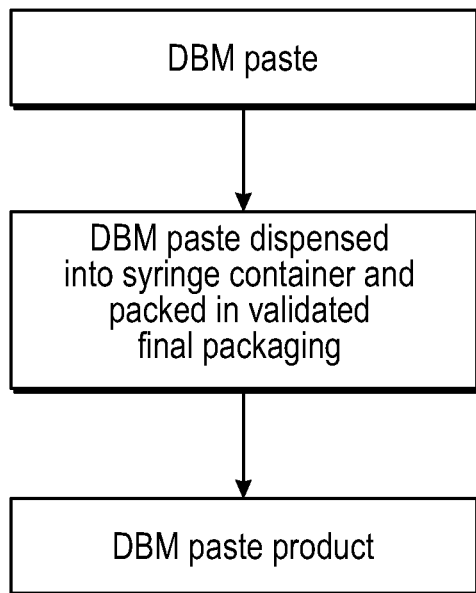
FIG. 8 is the subprocess of packaging taken from FIG. 3.
Figure 9:
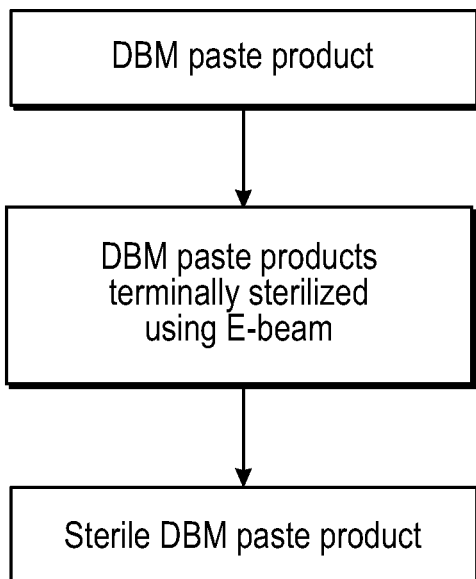
FIG. 9 is the subprocess of terminal sterilization using E-beam irradiation.

The subprocess shown in FIG. 8 is packaging. Capped syringes containing DBM aseptic paste products are packaged in validated final packaging. After final packaging, the product is terminally sterilized using E-beam irradiation as shown in FIG. 9. The packaged final products are stored at room temperature until they are distributed to the end user.

Other ranges of bone particle sized and mixture can be employed depending on the application which, in this example, was bone regeneration. Lower volumes may be more suited for less intrusive bone repairs or more if larger if larger amounts of material are needed as in a hip defect or repair.

It is understood, the exemplary process can be altered in terms of time, temperature, volume and material ratios and particle size distribution for a variety of adjustments to the paste or putty consistency. Ideally, the material achieved a low enough viscosity to be pushed through a syringe, but also can be made thick enough to retain its shape when molded like putty as the composition 10 in FIG. 1 shaped like a ball.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making a malleable demineralized bone composition consisting of cortical bone, comprising the steps of
   a) preparing cortical bone by cutting the cortical bone into pieces, freeze-drying the pieces and then grinding into particles and demineralizing the ground particles and freeze-drying the demineralized ground particles to form freeze-dried demineralized bone matrix (DBM) particles;
   b) dividing the freeze-dried DBM particles into a first portion and a second portion;
   c) autoclaving a volume of the second portion of DBM particles mixed with sterile water to form a gelatin;
   d) cooling the gelatin; and
   e) mixing the freeze-dried ground particles of the first portion with the gelatin from the second portion at a ratio of 80:20 or less gelatin to DBM to create a malleable and cohesive putty or paste, wherein the malleable and cohesive putty or paste is moldable into different shapes with no visible cracks and maintains its shape while immersed in normal saline or water for a minimum of one minute.

2. A method of making a malleable demineralized bone composition consisting of cortical bone comprising:
   a) preparing a first portion of cortical bone by cutting the cortical bone into pieces, freeze-drying the pieces and then grinding into particles and demineralizing the ground particles and thereafter freeze-drying the demineralized ground particles to form a first portion of demineralized bone matrix (DBM) particles;
   b) preparing a second portion of cortical bone by shaving cortical bone plates cut into 6.5 cm long pieces, wherein cortical bone is cut into long pieces from the cortical bone plates, cleaned and then shaved to form shavings of cortical bone tissue then freeze-drying the shavings, grinding the freeze-dried shavings to obtain a particle size less than 150 µm, and demineralizing the particles thereafter freeze-drying to form a second portion of DBM particles;
   c) autoclaving a volume of the second portion of DBM particles mixed with sterile water to form a gelatin;
   d) cooling the gelatin made from the second portion; and
   e) mixing the freeze-dried ground particles of the first portion with the gelatin from the second portion at a ratio of 80:20 or less gelatin to DBM to create a malleable and cohesive putty or paste, wherein the malleable and cohesive putty or paste is moldable into different shapes with no visible cracks and maintains its shape while immersed in normal saline or water for a minimum of one minute.

* * * * *